(12) United States Patent
Murugesan et al.

(10) Patent No.: US 12,201,599 B2
(45) Date of Patent: Jan. 21, 2025

(54) COMPOSITIONS AND METHODS FOR INHIBITING BLOOD CANCER CELL GROWTH

(71) Applicants: University of New Brunswick, Fredericton (CA); Université de Moncton, Moncton (CA)

(72) Inventors: Alli Murugesan, Saint John (CA); Anthony Reiman, Saint John (CA); Mohamed Touaibia, Dieppe (CA)

(73) Assignee: THE UNIVERSITY OF NEW BRUNSWICK UNIVERSITÉ DE MONCTON, Fredericton (CA)

( * ) Notice: Subject to any disclaimer, the term of this patent is extended or adjusted under 35 U.S.C. 154(b) by 598 days.

(21) Appl. No.: 16/757,595

(22) PCT Filed: Oct. 22, 2018

(86) PCT No.: PCT/CA2018/000198
§ 371 (c)(1),
(2) Date: Apr. 20, 2020

(87) PCT Pub. No.: WO2019/075549
PCT Pub. Date: Apr. 25, 2019

(65) Prior Publication Data
US 2020/0268700 A1 Aug. 27, 2020

Related U.S. Application Data

(60) Provisional application No. 62/575,136, filed on Oct. 20, 2017.

(51) Int. Cl.
| | |
|---|---|
| *A61K 31/519* | (2006.01) |
| *A61K 31/216* | (2006.01) |
| *A61K 31/497* | (2006.01) |
| *A61K 31/506* | (2006.01) |
| *A61K 31/555* | (2006.01) |
| *A61K 45/06* | (2006.01) |
| *A61P 35/00* | (2006.01) |

(52) U.S. Cl.
CPC ............ *A61K 31/216* (2013.01); *A61P 35/00* (2018.01)

(58) Field of Classification Search
CPC .. A61K 31/216; A61K 31/519; A61K 31/555; A61K 31/506; A61K 31/497; A61K 39/3955; A61K 39/39558; A61K 39/39566; A61K 45/06; A61K 2300/00; A61K 2039/505; A61P 35/00; A61P 35/02; C07C 69/732; C07K 16/2818
See application file for complete search history.

(56) References Cited

U.S. PATENT DOCUMENTS

| | | |
|---|---|---|
| 5,981,583 A | 9/1999 | Aggarwal et al. |
| 8,450,337 B2 | 5/2013 | Priebe et al. |
| 2017/0042865 A1 | 2/2017 | Zaid et al. |

FOREIGN PATENT DOCUMENTS

| | | | |
|---|---|---|---|
| CN | 107157978 | | 9/2017 |
| JP | 2003119169 | | 4/2003 |
| JP | 2010180167 | * | 1/2010 |
| WO | 2017147718 | | 9/2017 |

OTHER PUBLICATIONS

Etzenhouser et al., Bioorg. Med. Chem., 2001, 9, 199-209.*
JP2010180167-machine-translation, 2010, machine translation of JP2010180167.*
Zhu YX, Kortuem KM, Stewart AK. Molecular mechanism of action of immune-modulatory drugs thalidomide, lenalidomide and pomalidomide in multiple myeloma. Leuk Lymphoma. 2013; 54: 683-687.
Marin, E.H. and Wang, X. Anti-Cancer Effect of Fluorinated Caffeic Acid Phenethyl Ester on Multiple Myeloma Cells. The FASEB Journal, vol. 31, No. 1, Supplement Ib533. Apr. 2017.
Boudreau LH, Maillet J, LeBlanc LM, Jean-Francois J, Touaibia M, et al. (2012) Caffeic Acid Phenethyl Ester and Its Amide Analogue Are Potent Inhibitors of Leukotriene Biosynthesis in Human Polymorphonuclear Leukocytes. PLoS One 7(2): e31833. doi:10.1371/journal.pone.0031833.
Etzenhouser, B. et al. "Mechanism of Toxicity of Esters of Caffeic and Dihydrocaffeic Acids", Bioorganic & Medicinal Chemistry (2001), 9:199-209.
Sanderson, J.T. et al. "Antiproliferative, antiandrogenic and cytotoxic effects of novel caffeic acid derivatives in LNCaP human androgen-dependent prostate cancer cells", Bioorganic & Medicinal Chemistry (2013), 21:7182-7193.
Beauregard, A-P. et al. "CAPE Analogs Induce Growth Arrest and Apoptosis in Breast Cancer Cells", Molecules (2015), 20:12576-12589.
International Search Report and the Written Opinion of the International Searching Authority for PCT/CA2018/000198, Feb. 15, 2019.
Koru, O. et al. "Cytotoxic effects of caffeic acid phenethyl ester (CAPE) on the human multiple myeloma cell line", Turk J. Med Sci (2009), 39:863-870.
International Search Report of the International Searching Authority for PCT/CA2021/050339, Apr. 15, 2021.
Written Opinion of the International Searching Authority for PCT/CA2021/050339, Apr. 15, 2021.

(Continued)

*Primary Examiner* — Sun Jae Yoo
(74) *Attorney, Agent, or Firm* — Eugene Derenyi; Fogler, Rubinoff LLP (57) ABSTRACT

Methods, compositions and uses for inhibiting the growth in blood cancer cells with one or more of caffeic acid (3,4-dihydroxycinnamic acid) phenethyl ester (CAPE), CAPE analogue MT30, and CAPE analogue GL8. The blood cancer cells can be myeloma, lymphoma and leukemia cells. The methods, compositions and uses can be in conjunction with the use of an IMiD to treat a patient. The compositions can include a pharmaceutically acceptable carrier, adjuvant or vehicle, a pharmaceutically acceptable salt or dietary supplement.

17 Claims, 6 Drawing Sheets

(56) References Cited

OTHER PUBLICATIONS

Akyol et al., "In Vivo and In Vitro Antineopastic Actions of Caffeic Acid Phenethyl Ester (CAPE): Therapeutic Perspectives", Nutrition and Cancer, 2013, vol. 65, No. 4, pp. 515-526, ISSN 0163-5581.
Omene et al., "Propolis and its Active Component, Caffeic Acid Phenethyl Ester (CAPE), Modulate Breast Cancer Therapeutic Targets via an Epigenetically Mediated Mechanism of Action", J. of Cancer Sci Ther, 2013, vol. 5, No. 10, pp. 334-342, ISSN 1948-5956.
Chen Hui-Zhen et al., "Synthesis and antitumor activity of feruloyl and caffeoyl derivatives", Bioorganic & Medical Chemistry Letters, vol. 24. No. 18, Sep. 1, 2014, pp. 4367-4371.
Nagaoka T et al., "Selective antiproliferative activity of caffeic acid phenethyl ester analogues on highly liver-Metastatic murine colon 26-L5 carcinoma cell line", Bioorganic & Medical Chemistry, Elsevier, Amsterdam, NL, vol. 10, No. 10, Jan. 1, 2002, pp. 3351-3359.
Jeremie A. Doiron et al: "Structure-activity relationship of caffeic acid phenethyl ester analogs as new 5-lipoxygenase inhibitors", Chemical Biology & Drug Design, vol. 89, No. 4, Nov. 15, 2016, pp. 514-528.
Elizabeth Hernandez Marin et al: "Anti-Cancer Effect of Fluorinated Caffeic Acid Phenethyl Ester on Multiple Myeloma Cells—marin—2017—The FASEB Journal—Wiley Online Library", The Faseb Journal, Oct. 3, 2018, p. 1b533.
My Lien Jackson et al: "inhibitory effects of caffeic acid phenethyl ester (CAPE) derivatives on multiple myeloma cell growth—Jackson—2019—The FASEB Journal—Wiley Online Library", The Faseb Journal, Apr. 1, 2019, p. 816.13.
Chen J-H et al.: "Inhibitory effect of caffeic acid phenethyle ester on human leukemia HL-60 cells", Cancer Letters, New York, NY, US, vol. 108, No. 2, Jan. 1, 1996, pp. 211-214.
Kurata a et al: "Enzymatic synthesis of caffeic acid phenethyl ester analogues in ionic liquid", Journal of Biotechnology, Elsevier, Amsterdam NL, vol. 148, No. 2-3.
European Search Report dated Dec. 21, 2022 for EP Application No. 20791750, national phase of on PCT/CA2020050523.
Qian, Yiping et al: "Structure-activity relationship for anti-haemolysis and cytotoxicity against HL-60 cells of caffeic acid phenethyl ester derivatives", Shengwu Wuli Xuebao (2010), 26(4), 294-300.
Verma R.P. et al. "An approach towards the quantitative structure-activity relationships of caffeic acid and its derivatives", Chembiochem (2004), 5(9), 1188-1195.
International Search Report of the International Searching Authority for PCT/CA2020/050523, Jun. 18, 2020.
Abdi J, Chen G, Chang H. (2013) Drug resistance in multiple myeloma: latest findings and new concepts on molecular mechanisms. Oncotarget: 4: 2186-2207.
Armutcu, F., Akyol, S., Ustunsoy, S., & Turan, F. F. (2015). Therapeutic potential of caffeic acid phenethyl ester and its anti-inflammatory and immunomodulatory effects (Review). Experimental and Therapeutic Medicine, 9(5), 1582-1588. http://doi.org/10.3892/etm.2015.2346.
Bai B, Wu S, Wang R, Xu J, and Chen L, Bone marrow IRF4 level in multiple myeloma: an indicator of peripheral blood Th17 and disease. Oncotarget, 2017, vol. 8, (49), pp. 85392-85400.
Bertrand E, Jouy N, Manier S, Fouquet G, Guidez S, Boyle E, Noel S, Tomowiak C, Herbaux C, Schraen S, Preudhomme C, Quesnel B, Poulain S and Leleu X, Role of IRF4 in resistance to immunomodulatory (IMid) compounds in Waldenstrom's macroglobulinemia. Oncotarget, 2017, vol. 8, (68), pp. 112917-112927.
Bjorklund CC, Ma W, Wang ZQ, Davis RE, Kuhn DJ, Kornblau SM, et al. Evidence of a role for activation of Wnt/beta-catenin signaling in the resistance of plasma cells to lenalidomide. J Biol Chem. 2011; 286: 11009-11020.
Boddicker, R. L., Kip, N. S., Xing, X., Zeng, Y., Yang, Z.-Z., Lee, J.-H., . . . Feldman, A. L. (2015). The oncogenic transcription factor IRF4 is regulated by a novel CD30/NF-κB positive feedback loop in peripheral T-cell lymphoma. Blood, 125(20), 3118-27. http://doi.org/10.1182/blood-2014-05-578575.
Chesi, M., et al., The t(4;14) translocation in myeloma dysregulates both FGFR3 and a novel gene, MMSET, resulting in IgH/MMSET hybrid transcripts. Blood, 1998a. 92(9): p. 3025-34.
Chesi, M., et al., Dysregulation of cyclin D1 by translocation into an IgH gamma switch region in two multiple myeloma cell lines. Blood, 1996. 88(2): p. 674-81.
Chesi, M., et al., Frequent dysregulation of the c-maf proto-oncogene at 16q23 by translocation to an Ig locus in multiple myeloma. Blood, 1998b. 91(12): p. 4457-63.
Do, T. N., Ucisik-Akkaya, E., Davis, C. F., Morrison, B. A., & Dorak, M. T. (2010). An intronic polymorphism of IRF4 gene influences gene transcription in vitro and shows a risk association with childhood acute lymphoblastic leukemia in males. Biochimica et Biophysica Acta, 1802(2), 292-300. http://doi.org/10.1016/j.bbadis.2009.10.015.
Fesen, M. R., Pommier, Y., Leteurtre, F., Hiroguchi, S., Yung, J., & Kohn, K. W. (1994). Inhibition of HIV-1 integrase by flavones, caffeic acid phenethyl ester (CAPE) and related compounds. Biochemical Pharmacology, 48(3), 595-608. Retrieved from http://www.ncbi.nlm.nih.gov/pubmed/7520698.
Greenberg, A., Walters, D., Kumar, S., Rajkumar V., Jelinek, D., Responsiveness of cytogenetically discrete human myeloma cell lines to lenalidomide: Lack of correlation with cereblon and interferon regulatory factor 4 expression levels. Eur J Haematol. Dec. 2013; 91(6): doi:10.1111/ejh.12192.
Lopez-Girona A, Mendy D, Ito T, Miller K, Gandhi AK, Kang J. (2012). Cereblon is a direct protein target for immunomodulatory and antiproliferative activities of lenalidomide and pomalidomide. Leukemia, 26: 2326-2335.
Hans, C. P., Weisenburger, D. D., Greiner, T. C., Gascoyne, R. D., Delabie, J., Ott, G., . . . Chan, W. C. (2004). Confirmation of the molecular classification of diffuse large B-cell lymphoma by immunohistochemistry using a tissue microarray. Blood, 103(1), 275-82. http://doi.org/10.1182/blood-2003-05-1545.
Hengeveld, P. J., & Kersten, M. J. (2015). B-cell activating factor in the pathophysiology of multiple myeloma: a target for therapy? Blood Cancer Journal, 5, e282. http://doi.org/10.1038/bcj.2015.3.
Iida, S., Rao, P. H., Butler, M., Corradini, P., Boccadoro, M., Klein, B., . . . Dalla-Favera, R. (1997). Deregulation of MUM1/IRF4 by chromosomal translocation in multiple myeloma. Nature Genetics, 17(2), 226-30. http://doi.org/10.1038/ng1097-226.
Ito T, Ando H, Suzuki T, Ogura T, Hotta K . . . Handa H. (2010) dentification of a primary target of thalidomide teratogenicity. Science. Mar. 12;327(5971):1345 50.
Jost, P. J., & Ruland, J. (2007). Aberrant NF-kappaB signaling in lymphoma: mechanisms, consequences, and therapeutic implications. Blood, 109(7), 2700-7. http://doi.org/10.1182/blood-2006-07-025809.
Klein, U., Casola, S., Cattoretti, G., Shen, Q., Lia, M., Mo, T., . . . Dalla-Favera, R. (2006). Transcription factor IRF4 controls plasma cell differentiation and class-switch recombination. Nature Immunology, 7(7), 773-82. http://doi.org/10.1038/ni1357.
Kyle, RA, Gertz, MA, Witzig, TE, et al. Review of 1027 patients with newly diagnosed multiple myeloma. Mayo Clinic Proceedings 2003;78(1):21-33.
Larki-Harchegani, A., Hemmati, A. A., Arzi, A., Ghafurian-Boroojerdnia, M., Shabib, S., Zadkarami, M. R., & Esmaeilzadeh, S. (2013). Evaluation of the Effects of Caffeic Acid Phenethyl Ester on Prostaglandin E2 and Two Key Cytokines Involved in Bleomycin-induced Pulmonary Fibrosis. Iranian Journal of Basic Medical Sciences, 16(7), 850-7. Retrieved from http://www.ncbi.nlm.nih.gov/pubmed/23997916.
Marriott JB, Muller G, Stirling D, Dalgleish AG. (2001) Immunotherapeutic and antitumour potential of thalidomide analogues. Expert Opin Biol Ther., Jul;1(4):675-82.
Matsui W, Wang Q, Barber JP, Brennan S, Smith BD, Borrello I, et al. Clonogenic multiple myeloma progenitors, stem cell properties, and drug resistance. Cancer Res. 2008; 68: 190-197.
Morgan GJ, Walker BA, Davies FE. (2012). The genetic architecture of multiple myeloma. Nat Rev Cancer, 12: 335-348.

(56) References Cited

OTHER PUBLICATIONS

Natarajan, K., Singh, S., Burke, T. R., Grunberger, D., & Aggarwal, B. B. (1996). Caffeic acid phenethyl ester is a potent and specific inhibitor of activation of nuclear transcription factor NF-kappa B. Proceedings of the National Academy of Sciences of the United States of America, 93(17), 9090-5. Retrieved from http://www.ncbi.nlm.nih.gov/pubmed/8799159.

Nishida, K., et al., The Ig heavy chain gene is frequently involved in chromosomal translocations in multiple myeloma and plasma cell leukemia as detected by in situ hybridization. Blood, 1997. 90(2): p. 526-34.

Odqvist, L., Sánchez-Beato, M., Montes-Moreno, S., Martín-Sánchez, E., Pajares, R., Sánchez-Verde, L., . . . Piris, M. A. (2013). NIK controls classical and alternative NF-κB activation and is necessary for the survival of human T-cell lymphoma cells. Clinical Cancer Research: An Official Journal of the American Association for Cancer Research, 19(9), 2319-30. http://doi.org/10.1158/1078-0432.CCR-12-3151.

Okutan, H., Ozcelik, N., Yilmaz, H. R., & Uz, E. (2005). Effects of caffeic acid phenethyl ester on lipid peroxidation and antioxidant enzymes in diabetic rat heart. Clinical Biochemistry, 38(2), 191-6. http://doi.org/10.1016/j.clinbiochem.2004.10.003.

Onori, P.; DeMorrow, S.; Gaudio, E.; Franchitto, A.; Mancinelli, R.; Venter, J.; Kopriva, S.; Ueno, Y.; Alvaro, D.; Savage, J.; et al. Caffeic acid phenethyl ester decreases cholangiocarcinoma growth by inhibition of NF-κB and induction of apoptosis. Int. J. Cancer 2009, 125, 565-576.

Patel, S. (2016). Emerging Adjuvant Therapy for Cancer: Propolis and its Constituents. Journal of Dietary Supplements, 13(3), 245-68. http://doi.org/10.3109/19390211.2015.1008614.

Rajkumar SV. Multiple myeloma: 2014 update on diagnosis, risk-stratification, and management. Am J Hematol 2014;89(10):998-1009.

Rajkumar SV, Hayman SR, Lacy MQ, Dispenzieri A Gertz MA. (2005) Blood. Combination therapy with lenalidomide plus dexamethasone (Rev/Dex) for newly diagnosed myeloma. Blood, Dec. 15;106(13):4050-3. Epub Aug. 23, 2005.

Ryu, D., Kim, H. J., Joung, J.-G., Lee, H.-O., Bae, J. S., Kim, S. J., . . . Kim, K. (2014). Comprehensive genomic profiling of IgM multiple myeloma identifies IRF4 as a prognostic marker. Oncotarget, 7(30). http://doi.org/10.18632/oncotarget.9478.

Saito, M., Gao, J., Basso, K., Kitagawa, Y., Smith, P. M., Bhagat, G., . . . Dalla-Favera, R. (2007). A signaling pathway mediating downregulation of BCL6 in germinal center B cells is blocked by BCL6 gene alterations in B cell lymphoma. Cancer Cell, 12(3), 280-92. http://doi.org/10.1016/j.ccr.2007.08.011.

Sanderson, J. T., Clabault, H., Patton, C., Lassalle-Claux, G., Jean-François, J., Paré, A. F., . . . Touaibia, M. (2013). Antiproliferative, antiandrogenic and cytotoxic effects of novel caffeic acid derivatives in LNCaP human androgen-dependent prostate cancer cells. Bioorganic & Medicinal Chemistry, 21(22), 7182-93. http://doi.org/10.1016/.bmc.2013.08.057.

Shaffer, A. L., Emre, N. C. T., Lamy, L., Ngo, V. N., Wright, G., Xiao, W., . . . Staudt, L. M. (2008). IRF4 addiction in multiple myeloma. Nature, 454(7201), 226-31. http://doi.org/10.1038/nature07064.

Shaughnessy, J., Jr., et al., Cyclin D3 at 6p21 is dysregulated by recurrent chromosomal translocations to immunoglobulin loci in multiple myeloma. Blood, 2001. 98(1): p. 217-23.

Shen, H., Yamashita, A., Nakakoshi, M., Yokoe, H., Sudo, M., Kasai, H., . . . Moriishi, K. (2013). Inhibitory effects of caffeic acid phenethyl ester derivatives on replication of hepatitis C virus. PloS One, 8(12), e82299. http://doi.org/10.1371/journal.pone.0082299.

Singhal S, Mehta J, Desikan R, Ayers D, Roberson P Barlogie B. (1999) Antitumor activity of thalidomide in refractory multiple myeloma. N Engl J Med. Nov. 18;341(21):1565-71.

Sy, L. B., Yang, L.-K., Chiu, C.-J., & Wu, W.-M. (2011). The immunoregulatory effects of caffeic acid phenethyl ester on the cytokine secretion of peripheral blood mononuclear cells from asthmatic children. Pediatrics and Neonatology, 52(6), 327-31. http://doi.org/10.1016/j.pedneo.2011.08.005.

Szliszka, E., Czuba, Z. P., Bronikowska, J., Mertas, A., Paradysz, A., & Krol, W. (2011). Ethanolic Extract of Propolis Augments TRAIL-Induced Apoptotic Death in Prostate Cancer Cells. Evidence-Based Complementary and Alternative Medicine: eCAM, 2011, 535172. http://doi.org/10.1093/ecam/nep180.

Toman I, Loree J, Klimowicz AC, Bahlis N, Lai R, Belch A, Pilarski L, Reiman T. (2011). Expression and prognostic significance of Oct2 and Bob1 in multiple myeloma: implications for targeted therapeutics. Leuk Lymphoma 52(4): 659-67. doi: 10.3109/10428194.2010.548535.

Turesson, I., et al., Patterns of improved survival in patients with multiple myeloma in the twenty-first century: a population-based study. Journal of clinical oncology : official journal of the American Society of Clinical Oncology, 2010. 28(5): p. 830-4.

Wang, L., Chu, K., Liang, Y., Lin, Y., & Chiang, B. (2010). Caffeic acid phenethyl ester inhibits nuclear factor-kappaB and protein kinase B signalling pathways and induces caspase-3 expression in primary human CD4+ T cells. Clinical and Experimental Immunology, 160(2), 223-32. http://doi.org/10.1111/j.1365-2249.2009.04067.x.

Wang L, Yao ZQ, Moorman JP, Xu Y, Ning S (2014) Gene Expression Profiling Identifies IRF4-Associated Molecular Signatures in Hematological Malignancies. PLoS One 9(9): e106788. doi:10.1371/journal.pone.0106788.

Wang L, Toomey NL, Diaz LA, Walker G, Ramos JC, et al. (2011) Oncogenic IRFs provide a survival advantage for EBV- or HTLV1-transformed cells through induction of BIC expression. J Virol 85: 8328-8337.

Watabe, M., Hishikawa, K., Takayanagi, A., Shimizu, N., & Nakaki, T. (2004). Caffeic acid phenethyl ester induces apoptosis by inhibition of NFkappaB and activation of Fas in human breast cancer MCF-7 cells. The Journal of Biological Chemistry, 279(7), 6017-26. http://doi.org/10.1074/jbc.M306040200.

Xu D, Zhao L, Del Valle L, Miklossy J, Zhang L (2008) Interferon regulatory factors 4 is involved in Epstein-Barr virus-mediated transformation of human B lymphocytes. J Virol 82: 6251-6258.

Yang Y, Shi J, Tolomelli G, Xu H, Xia J, Wang H. (2013). RARα2 expression confers myeloma stem cell features. Blood, 122: 1437-1447.

Zheng, W., Liu, D., Fan, X., Powers, L., Goswami, M., Hu, Y., . . . Wang, S. A. (2013). Potential therapeutic biomarkers in plasma cell myeloma: a flow cytometry study. Cytometry. Part B, Clinical Cytometry, 84(4), 222-8. http://doi.org/10.1002/cyto.b.21083.

\* cited by examiner

CA (Caffeic acid): X = O, R = H
CAPE: X = O, R = CH$_2$CH$_2$Ph
D19: X = NH, R = CH$_2$CH$_2$Ph
MT30: X = O, R = CH$_2$CH$_2$Cyclohexyl
GL8: X = O, R = CH$_2$CH$_2$CH$_2$Ph

COMPOSITIONS AND METHODS FOR INHIBITING BLOOD CANCER CELL GROWTH

FIELD

The present disclosure relates to compositions and methods for inhibiting blood cancer cell growth.

BACKGROUND

Multiple myeloma is the second most common hematological malignancy and a so far incurable bone marrow cancer. Approximately 1% of all cancers are multiple myeloma (MM) accounting for 2% of all cancer deaths (Kyle et al., 2003; Rajkumar, 2014). The hallmark of multiple myeloma is the transformation of terminally differentiated plasma cells committed to producing polyclonal antibodies into aberrantly proliferating malignant myeloma cells (MMCs) that produce only monoclonal antibodies. This dramatic dysregulation results in disease-related symptoms such as nephropathy and hyperviscosity along with other clinical manifestations such as anemia, extensive skeletal destruction and hypercalcemia (Hengeveld & Kersten, 2015).

The progression from plasma cells to malignant myeloma cells involves multiple genetic events including chromosomal translocations. 50-75% of myeloma patients exhibit chromosome translocations at the immunoglobulin heavy chain (IgH) locus that juxtapose oncogenes from the partner chromosome under the control of strong 3' IgH enhancer elements (Nishida et al., 1997; Turesson et al., 2010; Chesi et al., 1998a). Overexpression of various oncogenes such as FGFR3, MMSET, Cyclin D1, Cyclin D3, cMAF occur depending on the partner locus involved in the translocation. (Chesi et al., 1996; Chesi et al., 1998b; Shaughnessy et al., 2001). Elevated expression of OCT2, a key transcription factor involved in IgH translocations has been implicated as a poor prognostic factor and has been associated with reduced survival in MM patients (Toman et al., 2011). Interferon regulatory factor (IRF4) is an indispensable transcription factor for plasma cell differentiation and deregulation of MUM1/IRF4 by chromosomal translocation in multiple myeloma has been well documented in myeloma patients (Iida et al., 1997). IRF4 has been shown to control plasma cell differentiation and class-switch recombination for creation of functionally competent plasma cells in transgenic mice models (Klein et al., 2006). Overexpression of IRF4 has been linked to poor prognosis in multiple myeloma, especially in certain types of the disease, such as those involving 14q32 translocation (Iida et al., 1997) or Immunoglobulin M (Ryu et al., 2014). IRF4 promotes proliferation of EBV-transformed cells and deficiency of IRF4 leads to death of cells derived from different hematological malignancies (Xu et al., 2008; Shaffer et al., 2008; Wang et al., 2011), confirming the role of IRF4 in tumorigenesis of hematological malignancies (Wang et al., 2014).

The genetic heterogeneity of myeloma poses a great challenge for treatment of the disease. Current chemotherapeutics exhibit several adverse side effects that affect the quality of life of myeloma patients, as well as face the challenge of resistance by myeloma cells. This warrants the need for novel therapeutics for multiple myeloma. In the search for novel compounds for cancer treatment, natural products affecting cell survival and cancer cell death pathways have gained the interest of the scientific community (Natarajan et al., 1996; Watabe et al., 2004; Wang et al., 2010; Szliszka et al., 2011). Caffeic acid (3,4-dihydroxycinnamic acid) phenethyl ester (CAPE) is an active principle of propolis from honeybee hives and a structural analogue of flavonoids. It has been known to exhibit diverse biological potential such as anti-oxidant (Okutan & Uz, 2005), immunomodulatory (Larki-Harchegani et al., 2013; Sy et al 2011), anti-inflammatory (Armutcu & Turan, 2015), anti-viral (Fesen et al., 1994; Shen et al., 2013) and anti-tumor activities (Onori et al., 2009; Patel S., 2016).

SUMMARY OF THE DISCLOSURE

The present invention in certain embodiments relates to methods for inhibiting the growth of blood cancer cells comprising contacting the cells with a caffeic acid (3,4-dihydroxycinnamic acid) phenethyl ester (CAPE) analogue selected from the group consisting of MT30, and GL8, according to the formulae:

MT30: X = O, R = CH$_2$CH$_2$Cyclohexyl
GL8: X = O, R = CH$_2$CH$_2$CH$_2$Ph or a pharmaceutically acceptable salt thereof, in an amount effective to inhibit the growth. In one embodiment, the blood cancer cells are myeloma cells. In a further embodiment, the myeloma cells are immune-modulatory drug (IMiD) resistant. In a still further embodiment, the myeloma cells are lenalidomide resistant myeloma cells. In another embodiment, the blood cancer cells are lymphoma cells. In another embodiment, the blood cancer cells are leukemia cells.

The present invention in certain other embodiments relates to methods for inhibiting the growth of blood cancer cells in a patient comprising administering to a patient a therapeutically effective amount of a caffeic acid (3,4-dihydroxycinnamic acid) phenethyl ester (CAPE) analogue selected from the group consisting of MT30, and GL8, according to the formulae:

MT30: X = O, R = CH$_2$CH$_2$Cyclohexyl
GL8: X = O, R = CH$_2$CH$_2$CH$_2$Ph or a pharmaceutically acceptable salt thereof.

In one embodiment, the blood cancer cells are myeloma cells. In a further embodiment, the myeloma cells are immune-modulatory drug (IMiD) resistant. In a still further embodiment, the myeloma cells are lenalidomide-resistant myeloma cells. In another embodiment, the blood cancer cells are lymphoma cells. In a still further embodiment, the lymphoma cells are lenalidomide-resistant lymphoma cells. In another embodiment, the blood cancer cells are leukemia cells.

In another embodiment, a CAPE analogue selected from the group consisting of MT30, and GL8, is used in conjunction with an IMiD to treat a patient.

The present invention in certain other embodiments relates to compositions for inhibiting the growth of blood cancer cells including a therapeutically effective amount of a caffeic acid (3,4-dihydroxycinnamic acid) phenethyl ester (CAPE) analogue selected from the group consisting of MT30, and GL8, according to the formulae:

MT30: X = O, R = CH$_2$CH$_2$Cyclohexyl
GL8: X = O, R = CH$_2$CH$_2$CH$_2$Ph or a pharmaceutically acceptable salt thereof.

In one embodiment, the blood cancer cells are myeloma cells. In a further embodiment, the myeloma cells are immune-modulatory drug (IMiD) resistant. In a still further embodiment, the myeloma cells are lenalidomide resistant myeloma cells. In another embodiment, the blood cancer cells are lymphoma cells. In another embodiment, the blood cancer cells are leukemia cells. In certain embodiments, the composition is a pharmaceutical composition. In certain embodiments, the composition is a dietary supplement. In certain embodiments, the composition includes a carrier. In certain other embodiments, the carrier is a pharmaceutically acceptable carrier.

The present invention in certain embodiments relates to the use of a caffeic acid (3,4-dihydroxycinnamic acid) phenethyl ester (CAPE) analogue selected from the group consisting of MT30, and GL8, according to the formulae:

MT30: X = O, R = CH$_2$CH$_2$Cyclohexyl
GL8: X = O, R = CH$_2$CH$_2$CH$_2$Ph or a pharmaceutically acceptable salt thereof, for inhibiting the growth of blood cancer cells. In one embodiment, the blood cancer cells are myeloma cells. In a further embodiment, the myeloma cells are immune-modulatory drug (IMiD) resistant. In a still further embodiment, the myeloma cells are lenalidomide resistant myeloma cells. In another embodiment, the blood cancer cells are lymphoma cells. In another embodiment, the blood cancer cells are leukemia cells.

The present invention in certain embodiments relates a method of decreasing a cereblon pathway protein in a patient including administering to the patient a therapeutically effective amount of a caffeic acid (3,4-dihydroxycinnamic acid) phenethyl ester (CAPE) analogue selected from the group consisting of MT30, and GL8, according to the formulae:

MT30: X = O, R = CH$_2$CH$_2$Cyclohexyl
GL8: X = O, R = CH$_2$CH$_2$CH$_2$Ph or a pharmaceutically acceptable salt thereof, whereby blood cancer cell growth is inhibited. In one embodiment, the cereblon pathway protein is Ikaros. In another embodiment, cereblon pathway protein is IRF4.

The present invention in certain other embodiments relates to compositions for decreasing a cereblon pathway protein including a therapeutically effective amount of a caffeic acid (3,4-dihydroxycinnamic acid) phenethyl ester (CAPE) analogue selected from the group consisting of MT30, and GL8, according to the formulae:

MT30: X = O, R = CH$_2$CH$_2$Cyclohexyl
GL8: X = O, R = CH$_2$CH$_2$CH$_2$Ph or a pharmaceutically acceptable salt thereof.

In one embodiment, the cereblon pathway protein is Ikaros. In another embodiment, cereblon pathway protein is IRF4.

The present invention in certain embodiments relates the use of a caffeic acid (3,4-dihydroxycinnamic acid) phenethyl ester (CAPE) analogue selected from the group consisting of MT30, and GL8, according to the formulae:

MT30: X = O, R = CH$_2$CH$_2$Cyclohexyl
GL8: X = O, R = CH$_2$CH$_2$CH$_2$Ph

The present invention in certain embodiments relates to methods for inhibiting the growth of blood cancer cells comprising contacting the cells with a caffeic acid (3,4-dihydroxycinnamic acid) phenethyl ester (CAPE) analogue consisting of MT30 according to the formulae:

MT30: X = O, R = CH₂CH₂Cyclohexyl or a pharmaceutically acceptable salt thereof, in an amount effective to inhibit the growth. In one embodiment, the blood cancer cells are myeloma cells. In a further embodiment, the myeloma cells are immune-modulatory drug (IMiD) resistant. In a still further embodiment, the myeloma cells are lenalidomide resistant myeloma cells. In another embodiment, the blood cancer cells are lymphoma cells. In another embodiment, the blood cancer cells are leukemia cells.

or a pharmaceutically acceptable salt thereof, for decreasing a cereblon pathway protein. In one embodiment, the cereblon pathway protein is Ikaros. In another embodiment, cereblon pathway protein is IRF4.

The present invention in certain embodiments relates to methods for inhibiting the growth of blood cancer cells comprising contacting the cells with a caffeic acid (3,4-dihydroxycinnamic acid) phenethyl ester (CAPE) consisting of GL8, according to the formulae:

GL8: X = O, R = CH₂CH₂CH₂Ph or a pharmaceutically acceptable salt thereof, in an amount effective to inhibit the growth. In one embodiment, the blood cancer cells are myeloma cells. In a further embodiment, the myeloma cells are immune-modulatory drug (IMiD) resistant. In a still further embodiment, the myeloma cells are lenalidomide resistant myeloma cells. In another embodiment, the blood cancer cells are lymphoma cells. In another embodiment, the blood cancer cells are leukemia cells.

In certain aspects of the present invention, pharmaceutically acceptable compositions are provided, wherein these compositions comprise any of the compounds or a pharmaceutically acceptable salt thereof, as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need thereof is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Methods
Cell Culture:

Human myeloma cell line KMM1 was purchased from the Japanese Collection of Research Bioresources Cell Bank (JCBR, Japan). KMS-11 cells were a kind gift from Dr. David Hoskin's Laboratory, Halifax, NS, Canada. Myeloma cells were grown in RPMI-1640 media (Sigma Aldrich, USA) supplemented with 5% heat inactivated FBS (Gibco), 200 mM L-glutamine (Gibco), 5 mM HEPES and 1%

Penstrep (Sigma Aldrich, USA) in a 5% $CO_2$ incubator at 37° C. Cell lines were tested regularly for mycoplasma and kept free of contamination. All other chemicals were obtained from Sigma Aldrich, USA.

Inhibitors:

Caffeic acid phenethyl ester and its closely related analogues were synthesized as previously in Sanderson et al. 2013. Caffeic acid is used as a standard to evaluate the effect of its conversion into ester (CAPE) or amide (D19). The replacement of the phenyl moiety of CAPE with a cyclohexyl (MT30), as well as the addition of an additional methylene (GL8) were also investigated. Stock solutions of inhibitors were made using DMSO and were stored as small aliquots at −20° C. Working dilutions were freshly prepared using cell media on the day of the experiment.

Inhibition Studies:

Myeloma cells were seeded in 96 well plates at a density of $10^4$ cells/well in appropriate cell media. Following overnight incubation at 37° C., MM cells were treated for 48 hours with varying concentrations of CAPE and its closely related analogues and cell viability was determined by PrestoBlue assay (Invitrogen, ON) according to the manufacturer's protocol.

Immunoblotting/Western Blotting Analyses:

Total protein extract was obtained from KMM1 and KMS-11 cells treated with CAPE and its closely related analogues and concentration of proteins determined by the Bicinchoninic acid assay (BCA) method. Protein samples were then fractionated by sodium dodecyl sulfate polyacrylamide gel electrophoresis (SDS PAGE) and transferred electrophoretically to a polyvinylidene (PVDF) membrane. Blots were then blocked with 5% nonfat dry milk in tris (hydroxymethyl)aminomethane-buffered saline-tween (TBS-T) for 1 hour and then incubated overnight with goat polyclonal anti-IRF4 antibody; rabbit polyclonal anti-OCT2 antibody, rabbit polyclonal anti-Bob1 antibody (Santa Cruz Biotechnology, Santa Cruz, CA); mouse polyclonal anti-Cyclin D3 (Cell Signaling Technology, Whitby, ON) and mouse monoclonal anti-beta tubulin antibody (Abcam, Cambridge, MA). Detection of protein in PVDF membrane was performed using the chemiluminescence kit (Bio-Rad Laboratories, Hercules, CA).

Statistical Analyses

All experiments were done in triplicates for each condition and data presented as mean±SD. All statistical analyses were done using GraphPad Prism 6, two-way ANOVA and Bonferroni's multiple comparison test was used to determine significance between groups and <0.05 is considered statistically significant.

Results

Synthesis of Caffeic Acid Phenethyl Ester and its Closely Related Analogues

Figure 1:
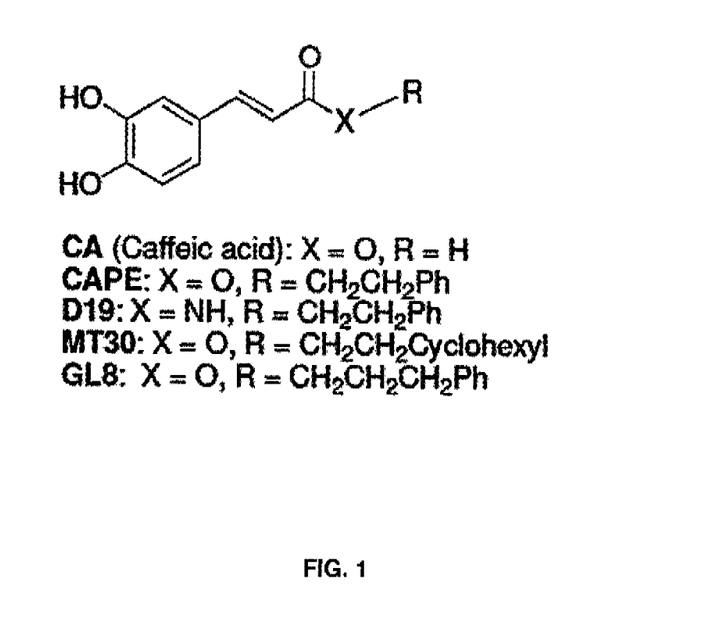
FIG. 1 depicts the chemical structure of Caffeic Acid Phenethyl Ester (CAPE) and related analogues MT30, GL8 and D19.

CAPE's derivatives (D19, MT30 and GL8) (FIG. 1) were synthesized as described previously (Sanderson et al. 2013).

Effect of CA Esters on the Viability of KMM1 Myeloma Cells

Figure 2:
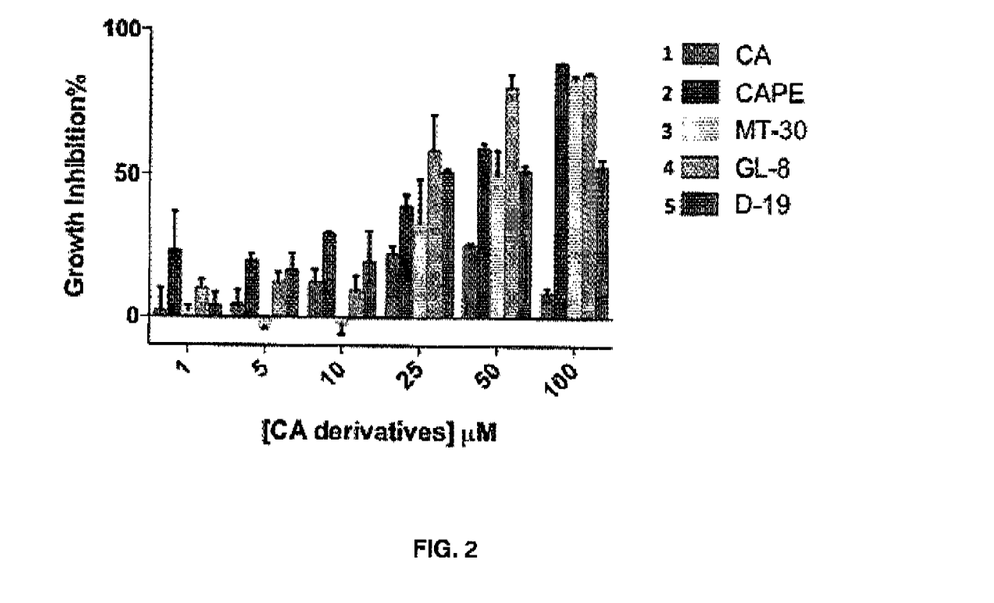
FIG. 2 is a bar graph depicting the effect of CAPE and related analogues MT30, GL8 and D19 on KMM1 cell growth.
Figure 2A:
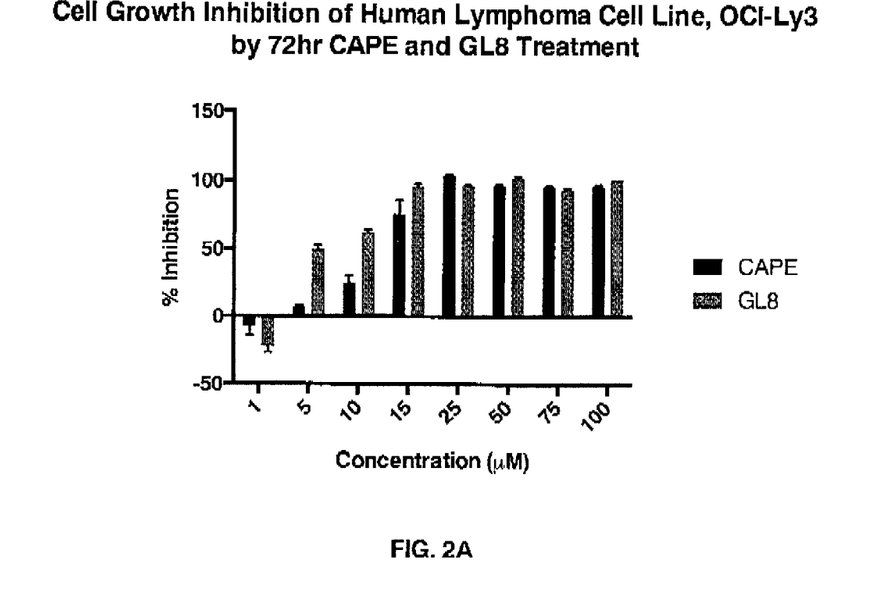
FIG. 2A is a bar graph showing the effect of GL8 in comparison to CAPE on a diffused large cell B-cell lymphoma cell line, OCI-Ly3.
Figure 2B:
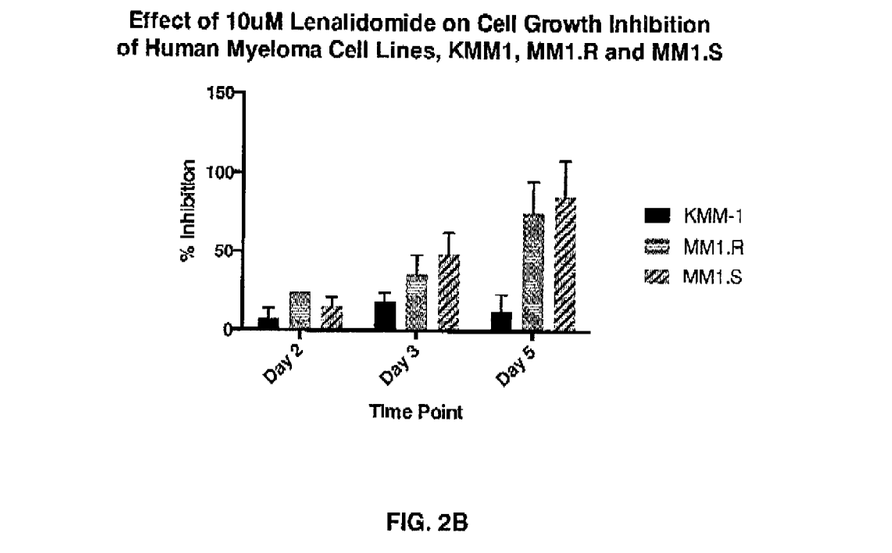
FIGS. 2B & 2C are histograms revealing the differential cell growth inhibition effect of lenalidomide on human myeloma cell lines—KMM1 (lenalidomide insensitive), MMIR (moderately sensitive to lenalidomide), MM1S (lenalidomide sensitive)
Figure 2C:
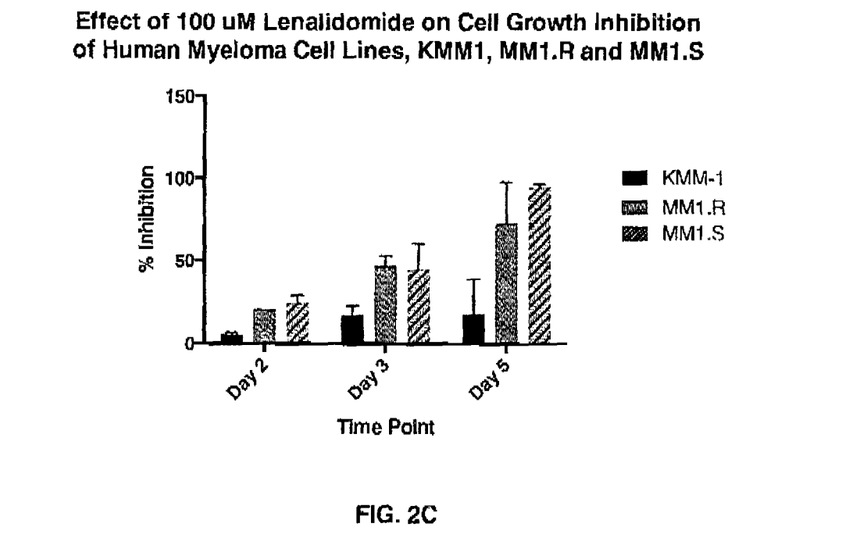
Figure 2D:
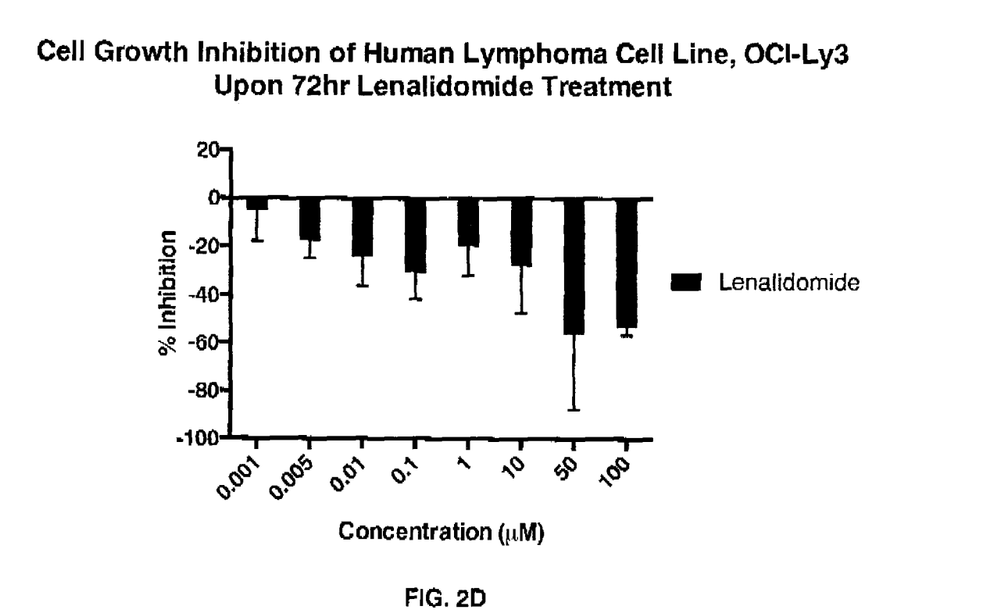
FIG. 2D is a bar graph depicting the effect of varying concentrations of lenalidomide on the cell growth of human lymphoma cell line—OCI-Ly3 (lenalidomide insensitive).

KMM1 myeloma cells were treated with varying concentrations of CAPE and its closely related analogues for 48 hours. At lower concentrations such as 1 µM, 5 µM and 10 µM, CAPE exhibited more myeloma growth inhibition compared to other analogues, however the myeloma cell growth inhibition was less than 30%. Interestingly, at 25 µM and 50 µM concentrations, GL8 showed significantly higher myeloma cell growth inhibition than CAPE and the other analogs. At 25 µM concentration, in comparison with CAPE that showed 38.7±4% growth inhibition, GL8 exhibited a significantly higher growth inhibition of 58.3±13% (P=0.002). At 50 µM, GL8 inhibited 80±5%, while CAPE inhibited the growth of 59.6±2% myeloma cells only (P=0.0008). Myeloma cell growth inhibition was determined by presto blue cell viability assay (FIG. 2). Another example demonstrates significantly higher lymphoma cell growth inhibition by GL8 in comparison with CAPE, in a lenalidomide non-responsive/insensitive human lymphoma cell line, OCI-Ly3 (FIG. 2A). At 5 µM, GL8 inhibited 49.9±2.9%, while CAPE inhibited the growth of 7.3±1% myeloma cells only (P=0.000017); At 10 µM, GL8 inhibited 62.3±2%, while CAPE inhibited the growth of 25.6±5% (P=0.00026). It is important to note that while CAPE exhibited a significant growth inhibition effect at higher concentrations such as 25 and 50 µM in myeloma cells, in the case of lymphoma cells, GL8 showed the growth inhibitory effect at concentrations as low as 5, 10 and 15 µM. FIG. 2A and FIG. 2D reveal that GL8 has a remarkable lymphoma cell growth inhibition effect on a diffused large B-cell Lymphoma (DLBCL) lymphoma cell line which is insensitive to lenalidomide.

Baseline Expression of IRF4 and Effect of CAPE and its Closely Related Analogues on IRF4, Caspase Protein Expression in Human Myeloma Cell Lines Cell lysates from human myeloma cell lines U266, KMS11, KMM1, JJN3 and the Epstein Barr Virus transformed B-lymphocyte cell line, IM9 were probed with anti-IRF4 antibodies by western blotting method.

Figure 3:
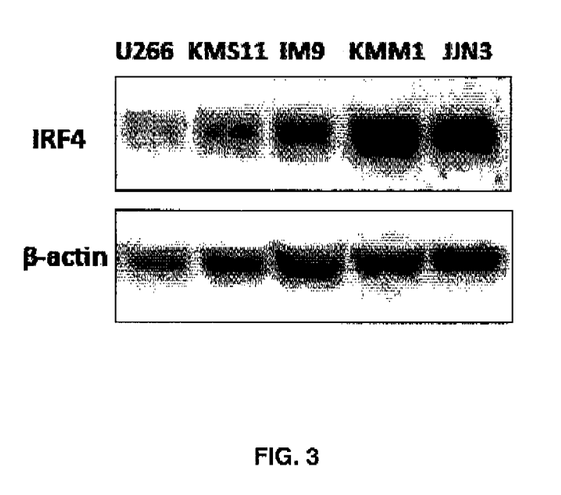
FIG. 3 is a representative image of an immunoblot showing the baseline expression of IRF4 proteins in human myeloma cell lines.

Protein extracts from human myeloma cell lines (HMCLs) such as U266, KMS11, KMM1, JJN3 and the Epstein Barr Virus transformed B-lymphocyte cell line, IM9 were subjected to SDS PAG electrophoresis on a 4-20% gradient gel, and the proteins were then transferred to a PVDF membrane. IRF4 protein expression in HMCLs was checked by western blotting method using the goat polyclonal IRF4 antibody, while beta-actin served as the protein loading control. Elevated expression of IRF4 was observed in KMM1 cell line when compared to other myeloma cell lines (FIG. 3).

Figure 4:
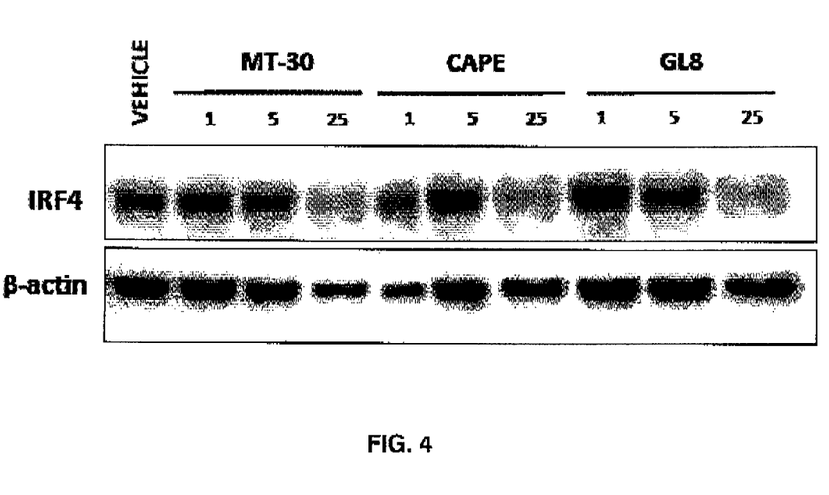
FIG. 4 is a representative image of an immunoblot showing the 48 hr treatment effect of CAPE and its closely related analogues on IRF4 protein levels of myeloma cells.

The two derivatives of CAPE, GL8 and MT30 that exhibited significant myeloma cell growth inhibition were tested for their effect on IRF4 expression in KMM1 cells. KMM1 cells were treated with 1, 5 and 25 µM of CAPE and its closely related analogues for 48 hours, cells were then harvested and proteins were extracted. 15 µg protein lysates were separated on a 4-20% gradient gel and then transferred to the PVDF membrane. The membrane was probed for IRF4 protein expression using affinity purified goat polyclonal antibody. Beta-actin was used as protein loading control. At 25 µM concentration, IRF4 protein expression was significantly down regulated by GL8 followed by MT30 and CAPE (at 25 µM concentration, CAPE decreased IRF4 protein expression level by 26% while the same concentration of GL8 decreased IRF4 levels by 62%) (FIG. 4). IRF4 inhibition via RNA interference led to myeloma cell death in ten different cell lines, suggesting that IRF4 may function as a master regulator to influence metabolic control, membrane biogenesis, cell cycle progression, cell death, cell differentiation, and transcription regulation (Shaffer et al., 2008). For the first time, the inventors have shown that CAPE and its analogues possess the novel biological activity of down-regulating IRF4 protein levels in blood cancers particularly in myeloma.

Figure 5:
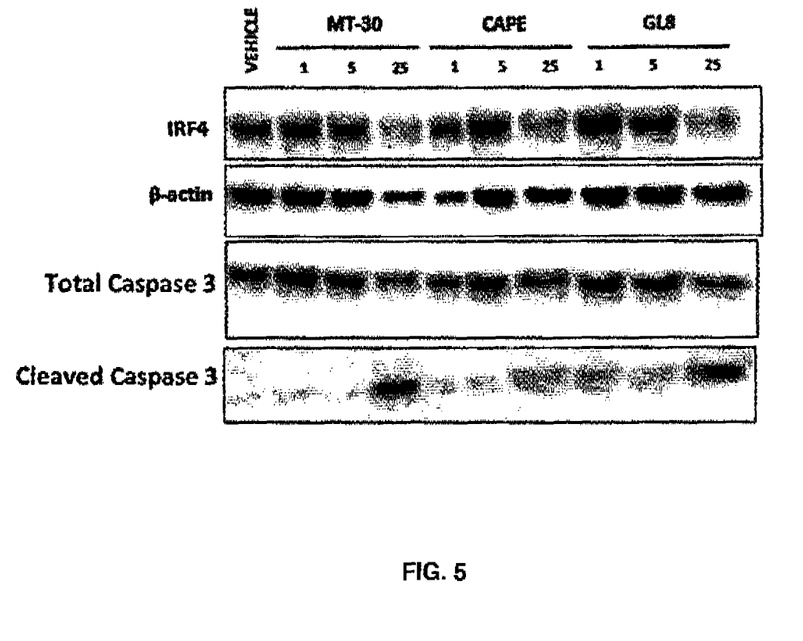
FIG. 5 is a representative image of an immunoblot showing the 48 hr treatment effect of CAPE and its closely related analogues on IRF4 and cleaved caspase protein levels of myeloma cells.

Furthermore, a noticeable increase in cleaved caspase levels in KMM1 cells treated with 25 µM GL8 and MT30 was observed. In comparison with 25 µM CAPE, a 3.2 fold increase in cleaved caspase-3 by MT30 and a 2.9 fold increase by 25 µM of GL8 were observed (FIG. 5).

Figure 6:
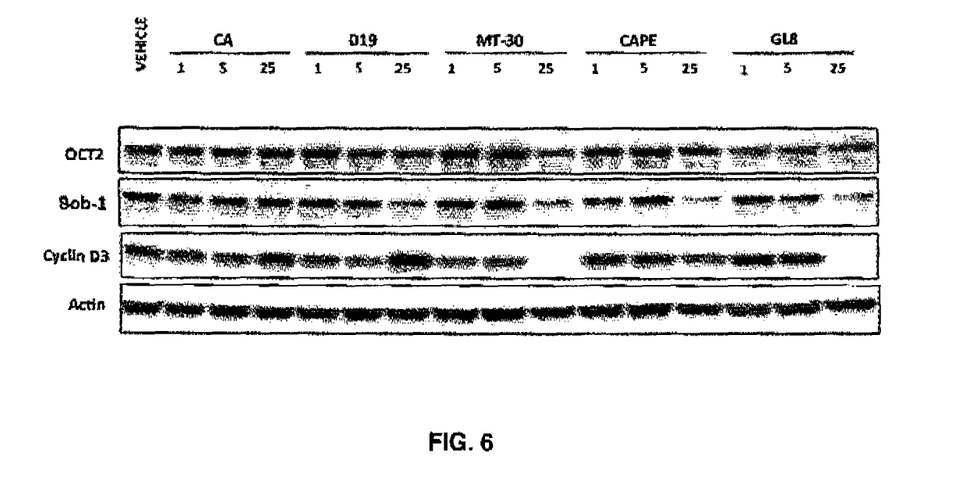
FIG. 6 is a representative image of an immunoblot showing the downstream effect of CAPE and its closely related analogues on Cyclin D3, OCT2 and Bob-1 protein levels in KMM1 myeloma cells; and, FIG. 7 is a representative image of an immunoblot showing the effect of Lenalidomide and CAPE analogues on Cereblon pathway proteins. Intensity of protein bands in the immunoblot was quantified by densitometry. Densitometry value for each protein is depicted in the image.

Effect of CAPE and its Closely Related Analogues on OCT2, Bob-1 and Cyclin D3 in KMM1 Cells As the KMM1 cells harbor t(6:14) chromosomal translocation that causes overexpression of the oncogene cyclin D3, the present inventors evaluated CAPE and its closely related analogues for their downstream effect on cyclin D3 protein levels, as well as on the protein targets such as OCT2, a key B-cell transcription factor and Bob-1, a co-activator involved in the IgH translocations of myeloma. The compounds CA and D19 did not have any effect on cyclin D3 levels. In comparison with CAPE, at 25 μM concentration, both GL8 and MT30 decreased cyclin D3 protein levels dramatically, while GL8 was found to decrease cyclin D3 levels in a dose-dependent manner. Also, OCT2 and Bob-1 protein levels were downregulated at higher concentration (25 μM) of CAPE, GL8 and MT30 (FIG. 6). CAPE and its closely related analogues at 1, 5 and 25 μM concentration were added to KMM1 cells for 48 hours, cells were harvested and proteins extracted. Protein lysates were then separated on a 4-20% gradient polyacrylamide gel and transferred to the PVDF membrane. The membrane was then probed sequentially using OCT2, Bob-1, Cyclin D3 and beta-actin antibodies.

Figure 7:
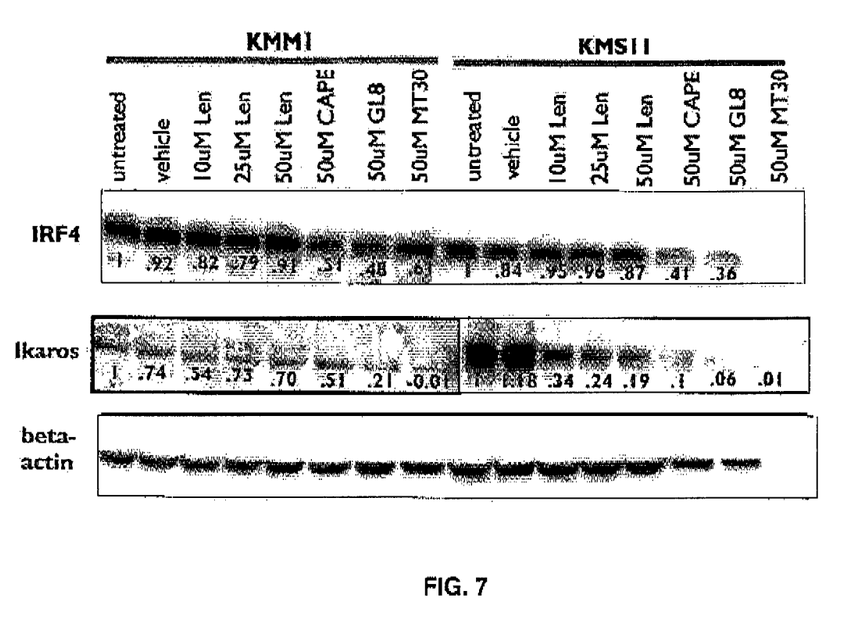

Effect of GL8 and MT30 in Comparison with the Standard Myeloma Drug Lenalidomide in Human Myeloma Cell Lines The present inventors checked the effect of lenalidomide and CAPE analogues on the lenalidomide-responsive myeloma cell line, KMS-11 and lenalidomide-resistant cell line KMM1. Neither the clinically relevant concentration of 10 μM lenalidomide (Greenberg et al., 2013) nor higher concentrations of lenalidomide (25 μM and 50 μM) tested had any effect on the IRF4 protein level in both lenalidomide responsive and resistant cell lines. Interestingly, in comparison with 50 μM CAPE, GL8 at the same concentration significantly decreased the levels of the cereblon pathway proteins, IRF4 and Ikaros in both lenalidomide responsive and resistant cell lines (FIG. 7). In the case of KMS-11 cells, lenalidomide decreased Ikaros levels in a dose-dependent manner but did not alter the levels of IRF4, and in comparison with 50 μM CAPE, GL8 significantly decreased the levels of Ikaros at the same concentration. Further examples reveal the differential cell growth inhibition effect of lenalidomide on human myeloma cell lines—KMM1 (lenalidomide insensitive), MMIR (moderately sensitive to lenalidomide), MM1S (lenalidomide sensitive) (FIGS. 2B & 2C); human lymphoma cell line—OCI-Ly3 (lenalidomide insensitive) (FIG. 2D).

Effect of Combination Treatment of Lenalidomide and CAPE Analogues on a Lenalidomide Non-Responsive Myeloma Cell Line, KMM1

The present inventors evaluated the effect of single compound treatment, as well as combination of CAPE analogues with lenalidomide in KMM1 cells. At the highest concentration of lenalidomide tested (100 μM), the cell viability was found to be at 78%, while single treatment of CAPE, MT30 and GL8 (25 μM) exhibited remarkable decrease in cell viability to 36%, 33% and 26% respectively. Interestingly the combination of the clinically relevant concentration of lenalidomide (10 μM) with 25 μM CAPE, MT30 and GL8 individually, further decreased the myeloma cell viability to 26%, 28.2% and 17.6%, respectively. Table 1 includes data on the effect of combination treatment of lenalidomide and CAPE analogues in lenalidomide non-responsive myeloma cell line, KMM1.

TABLE 1

| Lenalidomide (uM) | % KMM1 Cell viability after 72 hr Lenalidomide Treatment | 5 uM CAPE | 5 uM CAPE + Len | 5 uM MT30 | 5 uM MT30 + Len | 5 uM GL8 | 5 uM GL8 + Len | 25 uM CAPE | 25 uM CAPE + Len | 25 uM MT30 | 25 uM MT30 + Len | 25 uM GL8 | 25 uM GL8 + Len |
|---|---|---|---|---|---|---|---|---|---|---|---|---|---|
| 0.0001 | 99 | 51.8 | 51.7 | 39.6 | 41.8 | 45.0 | 46.5 | 36.0 | 28.1 | 33.2 | 34.6 | 26.1 | 24.2 |
| 0.0005 | 97 |  | 52.5 |  | 38.6 |  | 43.7 |  | 30.5 |  | 35.8 |  | 29.8 |
| 0.001 | 97 |  | 46.5 |  | 37.6 |  | 47.1 |  | 29.2 |  | 36.0 |  | 29.3 |
| 0.005 | 96 |  | 47.7 |  | 34.8 |  | 41.9 |  | 29.0 |  | 35.7 |  | 28.8 |
| 0.01 | 97 |  | 46.1 |  | 38.3 |  | 40.5 |  | 29.5 |  | 30.6 |  | 26.8 |
| 0.1 | 85 |  | 35.8 |  | 32.3 |  | 33.6 |  | 25.5 |  | 27.3 |  | 20.9 |
| 1 | 80 |  | 37.0 |  | 32.5 |  | 33.0 |  | 26.1 |  | 24.9 |  | 18.1 |
| 10 | 80 |  | 35.6 |  | 31.6 |  | 34.6 |  | 26.1 |  | 28.2 |  | 17.6 |
| 100 | 78 |  | 37.1 |  | 31.4 |  | 33.2 |  | 24.7 |  | 22.5 |  | 13.8 |

Cell Viability of Normal Mononuclear Cells after 48 hr CAPE and GL8 Treatment, Determined by Prestoblue Cell Viability Assay.

With reference to Table 2, neither GL8 nor CAPE at the following concentrations inhibited the cell growth of normal human bone marrow cells (mono nuclear cells) treated for 48 hrs.

TABLE 2

Normal Bone Marrow Mononuclear Cell Viability (%)

| Concentration (μM) | CAPE | | GL8 | | Vehicle (DMSO) | |
|---|---|---|---|---|---|---|
|  | Average | STD | Average | STD | Average | STD |
| 1 | 99.3 | 0.9 | 110.0 | 14.4 | 110.8 | 8.0 |
| 10 | 103.4 | 8.8 | 109.2 | 10.6 | 105.3 | 3.8 |
| 25 | 117.7 | 8.0 | 110.3 | 10.0 | 95.8 | 3.7 |
| 50 | 122.6 | 7.1 | 101.9 | 8.2 | 111.1 | 1.7 |

Discussion

Interferon regulatory factor 4 (IRF4) is a transcription factor critical for B cell development and function. IRF4 has been shown to control plasma cell differentiation and class-switch recombination in transgenic mice model (Klein et al., 2006). Overexpression of IRF4 has been linked to poor prognosis in multiple myeloma, especially in certain types of the disease, such as those involving 14q32 translocation (Iida et al., 1997) or Immunoglobulin M (Ryu et al., 2014). In most myelomas, IRF4 is not genetically altered (Shaffer et al., 2008). However, Shaffer et al., (2008), has demonstrated that IRF4 directly targets genes, including MYC, SCD, SQLE, CCNC, and CDK6, that are associated with various regulatory network and signaling pathways implicated in multiple myeloma. In the same study, IRF4 inhibition via RNA interference killed 10 myeloma cell lines, suggesting that IRF4 may function as a master regulator to influence metabolic control, membrane biogenesis, cell cycle progression, cell death, cell differentiation, and transcription regulation (Shaffer et al., 2008). Recently, a novel CD30/NF-κB positive feedback loop has been reported to regulate the oncogenic transcription factor IRF4 (Boddicker et al., 2015). Myeloma patients with end-stage disease had significantly higher IRF4 levels than those patients with early-stage disease, and this indicates increased expression of IRF4 proteins is associated with poor outcome (Bai et al., 2017).

In human peripheral T-cell lymphomas (PTCLs), activation of CD30 was shown to promote the activity of NF-κB subunits, p52 and RelB, leading to increased IRF4 expression (Boddicker et al., 2015), IRF4 in turn upregulated CD30 expression creating a positive feedback loop that directly controls lymphocyte growth and differentiation (Boddicker et al., 2015), which may contribute to the poor overall survival rate associated with PTCLs. There seems to be a complex network of regulation at a molecular level. IRF4 promoter activity not only depends on its inherent NF-κB response element, but also the presence of extra IRF4 gene and intronic SNP (Do, Ucisik-Akkaya, Davis, Morrison, & Dorak, 2010). Unlike PTCLs, multiple myeloma and diffuse large B-cell lymphomas (DLBCL) infrequently express CD30 (Hans et al., 2004; Zheng et al., 2013). Myc, a separate protein upregulated by IRF4 and involved in similar positive feedback mechanism as CD30, controls IRF4 expression more strongly in myeloma cells compared to PTCLs (Boddicker et al., 2015). The specific NF-κB factors involved may differ as studies have demonstrated the role of RelA (p65) in multiple myeloma and DLBCL, (Saito et al., 2007), as opposed to the alternative NF-kB pathway in PTCLs. Nevertheless, activation of NF-kB pathway is universal to these hematological malignancies (Odqvist et al., 2013), and its interaction with IRF4 may play a critical role in the feedback loop for maintenance and regulation. NF-kB is already a well-established therapeutic target in lymphoid malignancies (Jost & Ruland, 2007), but may show idiosyncrasy in its efficacy. Without being bound by theory, it has been postulated that therapeutic responses to such drugs may depend on the activity and expression of IRF4 (Boddicker et al., 2015). Down-regulation of IRF4 by CAPE and its closely related analogues may promote the sensitization of malignant cells to the effects of NF-kB-targeted therapies, leading to better clinical outcomes.

The CAPE analogues GL8 and MT30 could also be used to treat conditions of immune-modulatory drugs (IMiDs) resistance encountered in myeloma. Thalidomide is the first of the IMiD class of drug that was found to be effective against multiple myeloma in 1999 (Singhal et al., 1999), while the second generation IMiDs, lenalidomide and pomalidomide demonstrated more potent anti-myeloma, anti-inflammatory and immunomodulatory activities (Marriot et al., 2001). Lenalidomide has been reported to be a highly effective drug for the treatment of myeloma (Rajkumar et al., 2005) and has activity in other B cell lymphomas. The biochemical mechanism underlying the therapeutic activity of IMiDs was unknown for a while, until recently when thalidomide was shown to bind to the protein cereblon (CRBN), which is the substrate-recognition component of a cullin-dependent E3 ubiquitin ligase, and inhibit its auto-ubiquitination activity (Ito et al., 2010), IMiDs are able to modify the substrate specificity of CRBN, and lenalidomide-bound cereblon acquires the ability to target for proteasomal degradation of two specific B-cell transcription factors, Ikaros family zinc finger proteins 1 and 3 (IKZF1 and IKZF3). Loss of IKZF1 (ikaros) and IKZF3 (aiolos) by lenalidomide treatment in two lenalidomide sensitive myeloma cell lines, MM1S and KMS34, was followed by a decrease in IRF4, acting downstream of IKZF1 and/or IKZF3 (Ito et al., 2010), thus leading to toxic outcome for multiple myeloma cells. We observed that in comparison with lenalidomide treated myeloma cells, GL8 treated cells exhibited a dramatic decrease in levels of the cereblon pathway proteins, Ikaros (IKZF1) and IRF4 in a lenalidomide resistant myeloma cell line, KMM1.

The complex genomic instability and cytogenetic constitution in myeloma predisposes malignant cells to intrinsic resistance. The genetic lesions such as inherited variations, translocations, copy number abnormalities, mutations, methylation and micro RNA abnormalities are associated with myeloma proliferation and drug resistance (Morgan et al., 2012; Abdi et al., 2013). In myeloma, cancer stem cells (CSCs) exhibit high levels of ABC activity, aldehyde dehydrogenases (ALDH1), and retinoic acid receptor α (RARα) that have been associated with clonogenic potential and resistance to chemotherapy (Matsui et al., 2008; Yang et al., 2013). Resistance to lenalidomide has been explored and reported to be mediated by the induction of the Wnt/β-catenin pathway (Bjorklund et al., 2011), and decreased expression of the cereblon protein (CRBN) in myeloma (Zhu et al., 2013; Lopez-Girona et al., 2012). Furthermore, high IRF4 levels have recently been identified as the potential mechanism of resistance to lenalidomide and pomalidomide in Waldenström's macroglobulinemia, a type of lymphoma (Bertrand et al., 2017).

REFERENCES

Abdi J, Chen G, Chang H. (2013) Drug resistance in multiple myeloma: latest findings and new concepts on molecular mechanisms. Oncotarget: 4: 2186-2207.

Armutcu, F., Akyol, S., Ustunsoy, S., & Turan, F. F. (2015). Therapeutic potential of caffeic acid phenethyl ester and its anti-inflammatory and immunomodulatory effects (Review). *Experimental and Therapeutic Medicine,* 9(5), 1582-1588. http://doi.org/10.3892/etm.2015.2346.

Bai B, Wu S, Wang R, Xu J, and Chen L, Bone marrow IRF4 level in multiple myeloma: an indicator of peripheral blood Th17 and disease. Oncotarget, 2017, Vol. 8, (49), pp: 85392-85400

Bertrand E, Jouy N, Manier S, Fouquet G, Guidez S, Boyle E, Noel S, Tomowiak C, Herbaux C, Schraen S, Preudhomme C, Quesnel B, Poulain S and Leleu X, Role of IRF4 in resistance to immunomodulatory (IMid) compounds in Waldenström's macroglobulinemia. Oncotarget, 2017, Vol. 8, (68), pp: 112917-112927.

Bjorklund C C, Ma W, Wang Z Q, Davis R E, Kuhn D J, Kornblau S M, et al. Evidence of a role for activation of Wnt/beta-catenin signaling in the resistance of plasma cells to lenalidomide. J Biol Chem. 2011; 286: 11009-11020.

Boddicker, R. L., Kip, N. S., Xing, X., Zeng, Y., Yang, Z.-Z., Lee, J.-H., . . . Feldman, A. L. (2015). The oncogenic transcription factor IRF4 is regulated by a novel CD30/NF-κB positive feedback loop in peripheral T-cell lymphoma. *Blood,* 125(20), 3118-27. http://doi.org/10.1182/blood-2014-05-578575

Chesi, M., et al., The t(4;14) translocation in myeloma dysregulates both FGFR3 and a novel gene, MMSET, resulting in IgH/MMSET hybrid transcripts. Blood, 1998a. 92(9): p. 3025-34.

Chesi, M., et al., Dysregulation of cyclin D1 by translocation into an IgH gamma switch region in two multiple myeloma cell lines. Blood, 1996. 88(2): p. 674-81.

Chesi, M., et al., Frequent dysregulation of the c-maf proto-oncogene at 16q23 by translocation to an Ig locus in multiple myeloma. Blood, 1998b. 91(12): p. 4457-63.

Do, T. N., Ucisik-Akkaya, E., Davis, C. F., Morrison, B. A., & Dorak, M. T. (2010). An intronic polymorphism of IRF4 gene influences gene transcription in vitro and shows a risk association with childhood acute lymphoblastic leukemia in males. Biochimica et Biophysica Acta, 1802(2), 292-300. http://doi.org/10.1016/j.bbadis.2009.10.015.

Fesen, M. R., Pommier, Y., Leteurtre, F., Hiroguchi, S., Yung, J., & Kohn, K. W. (1994). Inhibition of HIV-1 integrase by flavones, caffeic acid phenethyl ester (CAPE) and related compounds. Biochemical Pharmacology, 48(3), 595-608. Retrieved from http://www.ncbi.nlm.nih.gov/pubmed/7520698.

Greenberg, A., Walters, D., Kumar, S., Rajkumar V., Jelinek, D., Responsiveness of cytogenetically discrete human myeloma cell lines to lenalidomide: Lack of correlation with cereblon and interferon regulatory factor 4 expression levels. Eur J Haematol. 2013 December; 91(6): doi:10.1111/ejh.12192.

Lopez-Girona A, Mendy D, Ito T, Miller K, Gandhi A K, Kang J. (2012). Cereblon is a direct protein target for immunomodulatory and antiproliferative activities of lenalidomide and pomalidomide. Leukemia, 26: 2326-2335.

Hans, C. P., Weisenburger, D. D., Greiner, T. C., Gascoyne, R. D., Delabie, J., Ott, G., . . . Chan, W. C. (2004). Confirmation of the molecular classification of diffuse large B-cell lymphoma by immunohistochemistry using a tissue microarray. Blood, 103(1), 275-82. http://doi.org/10.1182/blood-2003-05-1545

Hengeveld, P. J., & Kersten, M. J. (2015). B-cell activating factor in the pathophysiology of multiple myeloma: a target for therapy? Blood Cancer Journal, 5, e282. http://doi.org/10.1038/bcj.2015.3

Iida, S., Rao, P. H., Butler, M., Corradini, P., Boccadoro, M., Klein, B., . . . Dalla-Favera, R. (1997). Deregulation of MUM1/IRF4 by chromosomal translocation in multiple myeloma. Nature Genetics, 17(2), 226-30. http://doi.org/10.1038/ng1097-226.\

Ito T, Ando H, Suzuki T, Ogura T, Hotta K . . . Handa H. (2010) dentification of a primary target of thalidomide teratogenicity. Science. March 12; 327(5971):1345 50.

Jost, P. J., & Ruland, J. (2007). Aberrant NF-kappaB signaling in lymphoma: mechanisms, consequences, and therapeutic implications. Blood, 109(7), 2700-7. http://doi.org/10.1182/blood-2006-07-025809

Klein, U., Casola, S., Cattoretti, G., Shen, Q., Lia, M., Mo, T., . . . Dalla-Favera, R. (2006). Transcription factor IRF4 controls plasma cell differentiation and class-switch recombination. Nature Immunology, 7(7), 773-82. http://doi.org/10.1038/ni1357

Kyle, R A, Gertz, M A, Witzig, T E, et al. Review of 1027 patients with newly diagnosed multiple myeloma. Mayo Clinic Proceedings 2003; 78(1):21 33

Larki-Harchegani, A., Hemmati, A. A., Arzi, A., Ghafurian-Boroojerdnia, M., Shabib, S., Zadkarami, M. R., & Esmaeilzadeh, S. (2013). Evaluation of the Effects of Caffeic Acid Phenethyl Ester on Prostaglandin E2 and Two Key Cytokines Involved in Bleomycin-induced Pulmonary Fibrosis. Iranian Journal of Basic Medical Sciences, 16(7), 850-7. Retrieved from http://www.ncbi.nlm.nih.gov/pubmed/23997916.

Marriott J B, Muller G, Stirling D, Dalgleish A G. (2001) Immunotherapeutic and antitumour potential of thalidomide analogues. Expert Opin Biol Ther., July; 1(4):675-82.

Matsui W, Wang Q, Barber J P, Brennan S, Smith B D, Borrello I, et al. Clonogenic multiple myeloma progenitors, stem cell properties, and drug resistance. Cancer Res. 2008; 68: 190-197.

Morgan G J, Walker B A, Davies F E. (2012). The genetic architecture of multiple myeloma. Nat Rev Cancer, 12: 335-348.

Natarajan, K., Singh, S., Burke, T. R., Grunberger, D., & Aggarwal, B. B. (1996). Caffeic acid phenethyl ester is a potent and specific inhibitor of activation of nuclear transcription factor NF-kappa B. Proceedings of the National Academy of Sciences of the United States of America, 93(17), 9090-5. Retrieved from http://www.ncbi.nlm.nih.gov/pubmed/8799159.

Nishida, K., et al., The Ig heavy chain gene is frequently involved in chromosomal translocations in multiple myeloma and plasma cell leukemia as detected by in situ hybridization. Blood, 1997. 90(2): p. 526-34.

Odqvist, L., Sánchez-Beato, M., Montes-Moreno, S., Martín-Sánchez, E., Pajares, R., Sánchez-Verde, L., . . . Piris, M. A. (2013). NIK controls classical and alternative NF-κB activation and is necessary for the survival of human T-cell lymphoma cells. Clinical Cancer Research: An Official Journal of the American Association for Cancer Research, 19(9), 2319-30. http://doi.org/10.1158/1078-0432.CCR-12-3151.

Okutan, H., Ozcelik, N., Yilmaz, H. R., & Uz, E. (2005). Effects of caffeic acid phenethyl ester on lipid peroxidation and antioxidant enzymes in diabetic rat heart. Clinical Biochemistry, 38(2), 191-6. http://doi.org/10.1016/j.clinbiochem.2004.10.003.

Onori, P.; DeMorrow, S.; Gaudio, E; Franchitto, A.; Mancinelli, R.; Venter, J.; Kopriva, S.; Ueno, Y.; Alvaro, D.; Savage, J.; et al. Caffeic acid phenethyl ester decreases cholangiocarcinoma growth by inhibition of NF-κB and induction of apoptosis. Int. J. Cancer 2009, 125, 565-576.

Patel, S. (2016). Emerging Adjuvant Therapy for Cancer: Propolis and its Constituents. Journal of Dietary Supplements, 13(3), 245-68. http://doi.org/10.3109/19390211.2015.1008614

Rajkumar S V. Multiple myeloma: 2014 update on diagnosis, risk-stratification, and management. Am J Hematol 2014; 89(10):998-1009.

Rajkumar S V, Hayman S R, Lacy M Q, Dispenzieri A Gertz M A. (2005) Blood. Combination therapy with lenalidomide plus dexamethasone (Rev/Dex) for newly diagnosed myeloma. Blood, December 15; 106(13):4050-3. Epub 2005 Aug. 23.

Ryu, D., Kim, H. J., Joung, J.-G., Lee, H.-O., Bae, J. S., Kim, S. J., . . . Kim, K. (2014). Comprehensive genomic profiling of IgM multiple myeloma identifies IRF4 as a prognostic marker. Oncotarget, 7(30). http://doi.org/10.18632/oncotarget.9478

Saito, M., Gao, J., Basso, K., Kitagawa, Y., Smith, P. M., Bhagat, G., . . . Dalla-Favera, R. (2007). A signaling pathway mediating downregulation of BCL6 in germinal center B cells is blocked by BCL6 gene alterations in B cell lymphoma. *Cancer Cell*, 12(3), 280-92. http://doi.org/10.1016/j.ccr.2007.08.011

Sanderson, J. T., Clabault, H., Patton, C., Lassalle-Claux, G., Jean-François, J., Paré, A. F., . . . Touaibia, M. (2013). Antiproliferative, antiandrogenic and cytotoxic effects of novel caffeic acid derivatives in LNCaP human androgen-dependent prostate cancer cells. *Bioorganic & Medicinal Chemistry*, 21(22), 7182-93. http://doi.org/10.1016/j.bmc.2013.08.057

Shaffer, A. L., Emre, N. C. T., Lamy, L., Ngo, V. N., Wright, G., Xiao, W., . . . Staudt, L. M. (2008). IRF4 addiction in multiple myeloma. *Nature*, 454(7201), 226-31. http://doi.org/10.1038/nature07064.

Shaughnessy, J., Jr., et al., *Cyclin D3 at 6p21 is dysregulated by recurrent chromosomal translocations to immunoglobulin loci in multiple myeloma*. Blood, 2001. 98(1): p. 217-23.

Shen, H., Yamashita, A., Nakakoshi, M., Yokoe, H., Sudo, M., Kasai, H., . . . Moriishi, K. (2013). Inhibitory effects of caffeic acid phenethyl ester derivatives on replication of hepatitis C virus. *PloS One*, 8(12), e82299. http://doi.org/10.1371/journal.pone.0082299

Singhal S, Mehta J, Desikan R, Ayers D, Roberson P Barlogie B. (1999) Antitumor activity of thalidomide in refractory multiple myeloma. N Engl J Med. November 18; 341(21):1565-71.

Sy, L. B., Yang, L.-K., Chiu, C.-J., & Wu, W.-M. (2011). The immunoregulatory effects of caffeic acid phenethyl ester on the cytokine secretion of peripheral blood mononuclear cells from asthmatic children. *Pediatrics and Neonatology*, 52(6), 327-31. http://doi.org/10.1016/j.pedneo.2011.08.005

Szliszka, E., Czuba, Z. P., Bronikowska, J., Mertas, A., Paradysz, A., & Krol, W. (2011), Ethanolic Extract of Propolis Augments TRAIL-Induced Apoptotic Death in Prostate Cancer Cells. *Evidence-Based Complementary and Alternative Medicine: eCAM*, 2011, 535172. http://doi.org/10.1093/ecam/nep180

Toman I, Loree J, Klimowicz A C, Bahlis N, Lai R, Belch A, Pilarski L, Reiman T. (2011). Expression and prognostic significance of Oct2 and Bob1 in multiple myeloma: implications for targeted therapeutics. Leuk Lymphoma 52(4): 659-67. doi: 10.3109/10428194.2010.548535.

Turesson, I., et al., *Patterns of improved survival in patients with multiple myeloma in the twenty-first century: a population-based study*. Journal of clinical oncology: official journal of the American Society of Clinical Oncology, 2010. 28(5): p. 830-4.

Wang, L., Chu, K., Liang, Y., Lin, Y., & Chiang, B. (2010). Caffeic acid phenethyl ester inhibits nuclear factor-kappaB and protein kinase B signalling pathways and induces caspase-3 expression in primary human CD4+ T cells. *Clinical and Experimental Immunology*, 160(2), 223-32. http://doi.org/10.1111/j.1365-2249.2009.04067.x Wang L, Yao Z Q, Moorman J P, Xu Y, Ning S (2014) Gene Expression Profiling Identifies IRF4-Associated Molecular Signatures in Hematological Malignancies. PLoS ONE 9(9): e106788. doi:10.1371/journal.pone.0106788.

Wang L, Toomey N L, Diaz L A, Walker G, Ramos J C, et al. (2011) Oncogenic IRFs provide a survival advantage for EBV- or HTLV1-transformed cells through induction of BIC expression. J Virol 85: 8328-8337.

Watabe, M., Hishikawa, K., Takayanagi, A., Shimizu, N., & Nakaki, T. (2004). Caffeic acid phenethyl ester induces apoptosis by inhibition of NFkappaB and activation of Fas in human breast cancer MCF-7 cells. *The Journal of Biological Chemistry*, 279(7), 6017-26. http://doi.org/10.1074/jbc.M306040200.

Xu D, Zhao L, Del Valle L, Miklossy J, Zhang L (2008) Interferon regulatory factors 4 is involved in Epstein-Barr virus-mediated transformation of human B lymphocytes. J Virol 82: 6251-6258.

Yang Y, Shi J, Tolomelli G, Xu H, Xia J, Wang H. (2013). RARα2 expression confers myeloma stem cell features. Blood, 122: 1437-1447.

Zheng, W., Liu, D., Fan, X., Powers, L., Goswami, M., Hu, Y., . . . Wang, S. A. (2013). Potential therapeutic biomarkers in plasma cell myeloma: a flow cytometry study. *Cytometry. Part B, Clinical Cytometry*, 84(4), 222-8. http://doi.org/10.1002/cyto.b.21083.

Zhu Y X, Kortuem K M, Stewart A K. Molecular mechanism of action of immune-modulatory drugs thalidomide, lenalidomide and pomalidomide in multiple myeloma. Leuk Lymphoma. 2013; 54: 683-687.

We claim:

1. A composition for inhibiting the growth of blood cancer cells comprising:

a therapeutically effective amount of a caffeic acid (3,4-dihydroxycinnamic acid) phenethyl ester (CAPE) analogue, according to the formulae:

MT30: X = O, R = CH$_2$CH$_2$Cyclohexyl wherein the blood cancer cells are not leukemia cells, and wherein the caffeic acid (3,4-dihydroxycinnamic acid) phenethyl ester (CAPE) analogue is present in the range of 5 μM-25 μM.

2. The composition of claim 1, wherein the blood cancer cells are myeloma cells.

3. The composition of claim 2, wherein the myeloma cells are immune-modulatory drug (IMiD) resistant.

4. The composition of claim 2, wherein the myeloma cells are lenalidomide resistant.

5. The composition of claim 1, wherein the blood cancer cells are lymphoma cells.

6. The composition of claim 5, wherein the lymphoma cells are diffused large B-cell Lymphoma.

7. The composition of claim 1, wherein the composition is a pharmaceutical composition.

8. The composition of claim 7, the composition further comprising a pharmaceutically acceptable carrier.

9. A composition for inhibiting the growth of blood cancer cells comprising:

a therapeutically effective amount of a caffeic acid (3,4-dihydroxycinnamic acid) phenethyl ester (CAPE) analogue selected from the group consisting of MT30, and GL8, according to the formulae:

MT30: X = O, R = CH₂CH₂Cyclohexyl
GL8: X = O, R = CH₂CH₂CH₂Ph and further comprising a therapeutically effective amount of lenalidomide.

10. The composition of claim 9, wherein the caffeic acid (3,4-dihydroxycinnamic acid) phenethyl ester (CAPE) analogue is present at a concentration in the range of 5 μM-25 μM.

11. The composition of claim 9, wherein the lenalidomide is present at a concentration in the range of 0.001-100 μM.

12. The composition of claim 9, wherein the composition is a pharmaceutical composition.

13. The composition of claim 12, the composition further comprising a pharmaceutically acceptable carrier.

14. A composition for inhibiting the growth of blood cancer cells comprising:
a therapeutically effective amount of a caffeic acid (3,4-dihydroxycinnamic acid) phenethyl ester (CAPE) analogue according to the formulae:

GL8: X = O, R = CH₂CH₂CH₂Ph

15. The composition of claim 14, wherein the caffeic acid (3,4-dihydroxycinnamic acid) phenethyl ester (CAPE) analogue is present in the range of 5 μM-25 μM.

16. The composition of claim 14, wherein the composition is a pharmaceutical composition.

17. The composition of claim 16, the composition further comprising a pharmaceutically acceptable carrier.

\* \* \* \* \*